United States Patent

Storz et al.

[11] Patent Number: 6,042,593
[45] Date of Patent: Mar. 28, 2000

[54] SHAVING OR CUTTING INSTRUMENT

[75] Inventors: Karl Storz, deceased, late of Tuttlingen, Germany, by Sybill Storz-Reling, executrix; Pavel Novak, Schaffhausen, Switzerland; Simon Solingen, Los Angeles, Calif.

[73] Assignee: Storz Endoskop GmbH, Switzerland

[21] Appl. No.: 09/077,180

[22] PCT Filed: Nov. 20, 1996

[86] PCT No.: PCT/DE96/02213

§ 371 Date: Jul. 16, 1998

§ 102(e) Date: Jul. 16, 1998

[87] PCT Pub. No.: WO97/18745

PCT Pub. Date: May 29, 1997

[30] Foreign Application Priority Data

Nov. 20, 1995 [DE] Germany ............... 195 43 259
Aug. 16, 1996 [DE] Germany ............... 196 33 124

[51] Int. Cl.[7] .................................................. A61B 17/22
[52] U.S. Cl. ............................................ 606/159; 606/180
[58] Field of Search .................................. 606/159, 180, 606/170, 79; 128/305

[56] References Cited

U.S. PATENT DOCUMENTS

| 3,719,186 | 3/1973 | Merig, Jr. ................. | 128/305 |
|---|---|---|---|
| 4,649,919 | 3/1987 | Thimsen et al. .......... | 128/305 |
| 4,728,319 | 3/1988 | Masch ...................... | 604/22 |
| 4,729,763 | 3/1988 | Henrie ...................... | 604/22 |
| 4,733,660 | 3/1988 | Itzkan ...................... | 128/303 |
| 4,762,130 | 8/1988 | Fogarty et al. ........... | 128/344 |
| 4,883,474 | 11/1989 | Sheridan et al. ......... | 604/280 |
| 5,114,399 | 5/1992 | Kovalcheck .............. | 606/180 |
| 5,201,750 | 4/1993 | Hocherl et al. ........... | 606/180 |

*Primary Examiner*—Michael Buiz
*Assistant Examiner*—Jonathan D. Goldberg
*Attorney, Agent, or Firm*—St. Onge Steward Johnston & Reens LLC

[57] ABSTRACT

A cutting apparatus is provided with both a rotating inner blade and a stationary outer blade at its distal end and is connected to a drive unit disposed in the proximal region. The outer blade is spaced from the inner blade to form an irrigation passage through which an irrigation liquid is passed. A flushing duct is provided for fluid communication to the distal end. Additionally, a suction passage is provided to exhaust tissue particles.

15 Claims, 1 Drawing Sheet

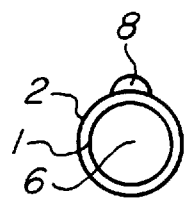
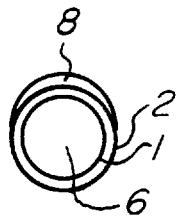
FIG. 1b          FIG. 1c
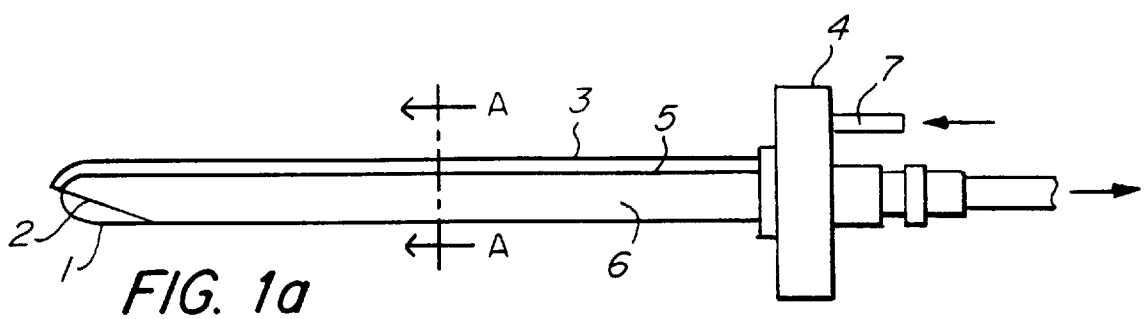
FIG. 1a
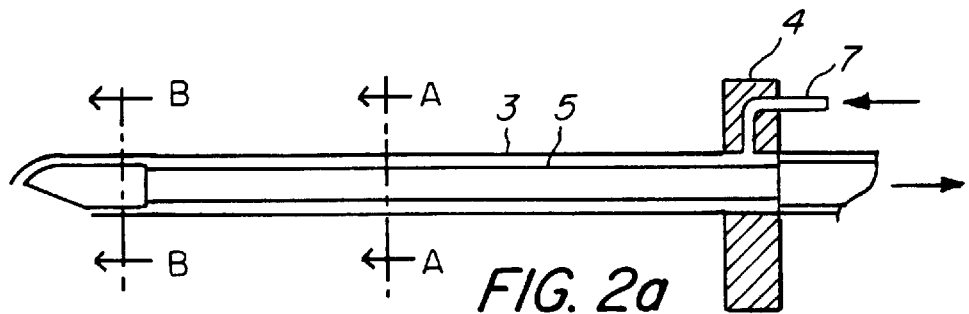
FIG. 2a
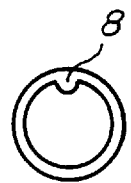   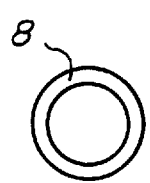
FIG. 2b          FIG. 2c
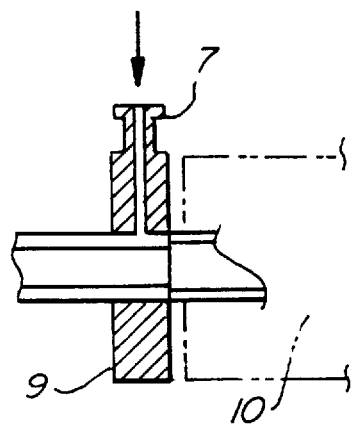
FIG. 3

SHAVING OR CUTTING INSTRUMENT

FIELD OF THE INVENTION

The present invention relates to an abrasive or cutting instrument with a rotating blade having an abrasive or cutting region at its distal end in accordance with the introductory clause of Patent claim 1.

Such abrasive or cutting instruments, which are also termed scrapers or rasps, are employed in endoscopic surgery, e.g. in micro arthroplasty operations.

PRIOR ART

Shaving or cutting instruments of the claimed general type include at least one blade which is rotated at a speed of up to 1,600 or more revolutions per minute. To this end the blade is connected via a shaft to a motor accommodated in the proximal section of the instrument.

The shaft may be a hollow shaft. The passage formed by this configuration is connected to a suction opening in the face area of the blades, which present normally a cylindrical configuration. In this manner it is possible to exhaust liquid and severed tissue particles through the blade.

The known removal or cutting instruments involve, however, the problem that abraded or cut-off tissue particles may adhere to the blade and hence induce the risk of soiling, of blade "clogging" and/or transfer of tissue particles.

BRIEF DESCRIPTION OF THE INVENTION

The present invention is based on the problem of improving an abrasive or cutting instrument in accordance with the introductory clause of claim 1 in a way that tissue particles will be prevented from adhering to the blade.

One inventive solution to this problem is defined in Patent claim 1. Improvements of the invention are the subject matters of the claims 2 et seq.

In accordance with the invention an additional irrigation passage is provided through which an irrigation or flushing liquid is passed to the distal end for cleaning the blade and for assistance in exhausting the severed or abraded tissue particles. It is preferred that the irrigation liquid does not enter the body cavity into which the instrument is introduced but is rather exhausted again immediately after it has rinsed and thus cleaned the blade (claim 11).

The inventive instrument is thus suitable for application not only in organs filled with an irrigating liquid, as is the case in arthroscopy, but also in body regions which can or should not be filled with the irrigating liquid. The inventive instrument can hence be used in ENT surgery, e.g. in the region of the nasal cavity.

The irrigation passage, which is provided in accordance with the invention, does not only serve to clean the blade but it reduces also the risk of clogging in exhaust passages with small lumina which present a typical inside diameter of 1 to 3 mm in ENT applications.

In the improvement defined in claim 2 the suction passage is centrally arranged. There the suction passage may be provided particularly in the drive tube of the rotating blade.

In accordance with claim 3 a handpiece is provided which receives the drive unit and is designed, in particular, in a way that the operator will be able to use the inventive instrument in an ergonomic way.

The basic inventive idea to provide an additional irrigation passage in an abrasive or cutting instrument of the claimed general type may be applied, on principle, in instruments of any configuration whatsoever, e.g. in instruments provided only with a rotating blade. The fundamental inventive idea is particularly expedient, however, in instruments provided with a rotating inner blade and a stationary outer blade (claim 4). With these instruments it happens especially frequently that severed tissue particles become stuck in the narrow gap between the inner and outer blades. The claims 5 to 8 define various alternatives of the arrangement of the irrigation passage, For instance, the gap between the inner and outer blades may constitute the irrigation passage. This configuration presents the advantage that the gap is thus cleaned with a particularly high efficiency even though the increased expenditure in terms of structure might be a disadvantage. The alternatives defined in claims 6 and 7 have a design which is comparatively simple to realise.

In the solution defined in claim 8 a hollow shaft is provided into which the blade and the tube attached to it are so inserted that the irrigation passage is formed between the tube and the shaft. This solution does not only result in an instrument which is very easy to clean and to sterilise in particular but it permits also the retrofitting of existing instruments of the claimed general type.

In such a design the hollow shaft is preferably arranged in a way that the irrigation passage surrounds the blade and the tube in coaxial relationship (claim 9). The improvement set forth in clam 10, according to which the hollow shaft is detachably fastened on the handpiece, substantially facilitates the cleaning of the instrument.

The clogging risk is further reduced with a suction passage flaring from the distal end towards the proximal end (claim 12).

The fundamental inventive ideas may preferably be applied in an instrument in which the abrasive or cutting section is disposed laterally of the blade in a manner known per se, and in which the face of the hollow shaft extends obliquely along the direction of the longitudinal axis. The risk of blade clogging is particularly high in the known instruments of this type when there is no irrigation passage. In such an instrument the provision is moreover preferred that the outlet opening for the discharge of the irrigation liquid is so configured that at least the bulk volume of the irrigation liquid will be discharged in the region which is not used for abrasion or cutting (claims 14 and 15).

The claims 15 to 17 describe various alternatives of the connectors which are provided at the proximal end for connection of the suction and irrigation passages.

In the version in which the proximally disposed irrigation passage connector forms an angle of 90° relative to the longitudinal instrument axis (claim 17) it is preferred that the irrigation passage connector is provided ahead of the handpiece, seen in a direction towards the proximal end, so that the outer blade will be rotatable relative to the handpiece.

BRIEF DESCRIPTION OF THE DRAWINGS

The invention will be described in more details by exemplary embodiments in the following, with reference to the drawing wherein:

FIG. 1a is a cross-sectional view of a first embodiment of an inventive instrument;

FIGS. 1b and 1c show alternatives of the arrangement of the irrigation passage;

FIG. 2a is a cross-sectional view of a second embodiment of an inventive instrument;

FIGS. 2b and 2c are each a sectional view along line A—A or B—B in FIG. 2a; and

FIG. 3 shows the proximal region of a third embodiment of the invention.

DESCRIPTION OF EMBODIMENTS

The inventive instrument illustrated in FIG. 1a comprises an inner blade 1 and an outer blade 2 in a manner known per se. The outer blade 2 is stationary and in the embodiment shown here it is connected to a proximal body portion 4 of the instrument. The inner blade 1 is connected via a tube 5 supported for rotation to a drive unit which is not illustrated here and which rotates the inner blade 1 relative to the main body portion 4 and hence to the stationary outer blade 2. A suction or exhaust passage 6 is provided in the tube 5, which is connected by its distal end to an appropriate suction pump not illustrated here.

In the embodiment shown here an additional irrigation passage is provided through which an irrigation pump (not illustrated) pumps an irrigation liquid from a fitting 7 to the distal end. In the embodiment illustrated here the irrigation passage 8 is mounted on the tube 3 of the outer blade 2. FIGS. 1b and 1c, which illustrate a section taken at A—A in FIG. 1a, represent two possibilities for the arrangement of the irrigation passage 8.

FIG. 2a shows an alternative of the arrangement of the irrigation passage 8, with identical parts being identified by the same reference numerals as in FIG. 1. In the embodiment shown in FIG. 2a the irrigation passage 8 surrounds the tube 5 of the inner blade 1 in coaxial relationship FIGS. 2b and 2c show each a sectional view taken at A—A and B—B in FIG. 2a.

FIG. 3 is a view of the proximal region of an embodiment in which the fitting 7 for the irrigation passage is not disposed in parallel with the longitudinal instrument axis but at an angle of 90° relative to the longitudinal axis. The fitting 7, which may be designed as Luer lock fitting, for instance, is arranged here in a part 9 separated from the remaining instrument so that it may be rotated about the longitudinal instrument axis. The reference numeral 10 indicates schematically the handpiece with the motor for driving the inner blade.

The abrasive or cutting instrument with the inventive configuration is suitable for application in the same manner as conventional instruments in combination with the common endoscopic instruments.

It is claimed:

1. An instrument comprising a tube with a rotating blade at a distal end of said tube, and adapted for a drive unit at a proximate end of the instrument, a suction passage provided in said tube for exhausting tissue particles, a stationary blade spaced from said rotating blade and forming therewith an irrigation passage in said tube through which an irrigation liquid is passed to the distal end for cleaning the rotating blade and for assistance in exhausting tissue particles.

2. Instrument according to claim 1, characterised in that said suction passage is centrally arranged.

3. Instrument according to claim or, characterized in that a handpiece is provided in which a drive unit is accommodated.

4. Instrument according to claim 1, characterized in that said irrigation passage is disposed in the instrument in an asymmetrical arrangement with respect to an axis along which the rotating blade extends.

5. Instrument according to claim 1, characterized in that said irrigation passage is disposed on said outer blade.

6. Instrument according to claim 1, characterized in that a hollow shaft is provided into which said blade and the tube attached thereto are inserted so as to form said irrigation passage between said tube and said shaft.

7. Instrument according to claim 6, characterised in that said irrigation passage surrounds said blade and said tube in a coaxial relationship.

8. Instrument according to claim 6, characterized in that said hollow shaft is detachably fastened on said handpiece.

9. Instrument according to claim 6, characterized in that a cutting region is provided laterally on said blade, and that a face of said hollow shaft extends obliquely along the direction of a longitudinal axis.

10. Instrument according to claim 1, characterized in that said suction passage is flared from the distal towards the proximal end.

11. Instrument according to claim 1, characterized in that a discharge opening for the irrigation liquid is so designed that at least a bulk volume of the irrigation liquid is discharged in a region of said irrigation channel spaced from said distal end said tube.

12. An instrument comprising a tube with a rotating blade at a distal end of said tube, and adapted for a drive unit at a proximate end of the instrument, a suction passage provided in said tube for exhausting tissue particles, an irrigation passage provided in said tube through which an irrigation liquid is passed to the distal end for cleaning the blade and for assistance in exhausting tissue particle, and coaxial proximal connectors for said suction and irrigation passages.

13. Instrument according to claim 12, characterized in that the proximally provided connectors for said suction and irrigation passages are configured to be adjacent to each other.

14. Instrument according to claim 12, characterized in that the proximally provided connector for said irrigation passage extends at an angle of 90° relative to a longitudinal instrument axis.

15. Instrument according to claim 12, characterized in that said irrigation passage is provided ahead of the handpiece, seen in a direction towards the proximal end, so that the outer blade will be rotatable relative to the handpiece.

* * * * *

UNITED STATES PATENT AND TRADEMARK OFFICE
CERTIFICATE OF CORRECTION

PATENT NO. : 6,042,593
DATED : March 28, 2000
INVENTOR(S) : Karl Storz (deceased) et al.

It is certified that error appears in the above-identified patent and that said Letters Patent is hereby corrected as shown below:

Column 1,
Line 45, delete "(claim 11)".

Column 2,
Line 5, delete "(claim 4)".
Line 8, replace "5 to 8" with -- 1 and 4 to 6 --.
Line 14, replace "6" with -- 4 --.
Line 15, replace "7" with -- 5 --.
Line 16, replace "8" with -- 6 --.
Line 25, replace "9" with -- 7 --.
Line 26, replace "10" with -- 8 --.
Line 31, replace "12" with -- 10 --.
Line 43, replace "14 and 15" with -- 11 and 12 --.
Line 44, replace "15 to 17" with -- 12 to 14 --.
Line 49, replace "17" with -- 14 --.

Column 4,
Line 3 replace "or" with -- 1 --.

Signed and Sealed this

Fourteenth Day of September, 2004

JON W. DUDAS
*Director of the United States Patent and Trademark Office*